(12) United States Patent
Yamatomo et al.

(10) Patent No.: US 8,258,252 B2
(45) Date of Patent: Sep. 4, 2012

(54) SUSTAINED-RELEASE COMPOSITION AND PROCESS FOR PRODUCING THE SAME

(75) Inventors: Kazumichi Yamatomo, Kyoto (JP); Akiko Yamada, Kyoto (JP); Yoshio Hata, Hokkaido (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 457 days.

(21) Appl. No.: 11/960,114

(22) Filed: Dec. 19, 2007

(65) Prior Publication Data
US 2008/0108778 A1    May 8, 2008

Related U.S. Application Data

(62) Division of application No. 10/479,516, filed as application No. PCT/JP02/06526 on Jun. 28, 2002, now abandoned.

(30) Foreign Application Priority Data

Jun. 29, 2001 (JP) ................................. 2001-199462
Nov. 6, 2001 (JP) ................................. 2001-340980

(51) Int. Cl.
*C08G 67/00* (2006.01)
(52) U.S. Cl. .......................... 528/271; 528/491; 528/499
(58) Field of Classification Search .......................... None
See application file for complete search history.

(56) References Cited

U.S. PATENT DOCUMENTS

| | | | |
|---|---|---|---|
| 5,575,987 A | 11/1996 | Kamei et al. | |
| 5,585,460 A * | 12/1996 | Yamada et al. | 528/491 |
| 5,622,657 A | 4/1997 | Takada et al. | |
| 5,651,990 A | 7/1997 | Takada et al. | |
| 5,716,640 A | 2/1998 | Kamei et al. | |
| 6,740,634 B1 | 5/2004 | Saikawa et al. | |
| 7,388,032 B2 | 6/2008 | Saikawa et al. | |
| 2003/0134800 A1 | 7/2003 | Yamamoto et al. | |
| 2005/0214330 A1 | 9/2005 | Yamamoto et al. | |

FOREIGN PATENT DOCUMENTS

| | | |
|---|---|---|
| EP | 0 145 240 A2 | 6/1985 |
| EP | 0 171 907 * | 7/1985 |
| EP | 0 171 907 A1 | 2/1986 |
| EP | 0 190 833 A2 | 8/1986 |
| EP | 0 202 065 A2 | 11/1986 |
| EP | 0 452 111 A2 | 10/1991 |
| EP | 0 586 238 A2 | 3/1994 |
| EP | 0 633 020 A1 | 1/1995 |
| EP | 1 048 301 A1 | 11/2000 |
| JP | 4-218528 A | 8/1992 |
| JP | 6-192068 A | 7/1994 |
| JP | 11-269094 A | 10/1999 |
| JP | 2002-114667 A | 4/2002 |
| WO | WO 00/35990 A1 | 6/2000 |

OTHER PUBLICATIONS

Akaza et al., "Long-term Clinical Study on Luteinising Hormonereleasing Hormone Agonist Depot Formulation in the Treatment of Stage D Prostatic Cancer," Jpn. J. Clin. Oncol., 1992, 22(3)177-184. -

Extended European Search Report and European search opinion dated Sep. 14, 2009, in corresponding EP 09155256.2, 8 pages.

Okada et al., "Preparation of three-month depot injectable microspheres of leuprorelin acetate using biodegradable polymers," Pharmaceutical Research, Aug. 1, 1994, 11(8):1143-1147.

Kostanski J. W. et al., "Preparation, Characterization, and in Vitro Evaluation of 1- and 4-Month Controlled Release Orntide PLA and PLGA Microspheres," Pharmaceutical Development and Technology, vol. 5, No. 4, 2000, pp. 585-596, XP009001300.

Ogawa Y. et al., "Controlled-Release of Leuprolide Acetate from Polylactic Acid or Copoly-Lactic-Glycolic Acid Microcapsules Influence of Molecular Weight and Copolymer Ratio of Polymer," Chemical & Pharmaceutical Bulletin, vol. 36, No. 4, 1988, pp. 1502-1507, XP001120337.

Takenaga M. et al., "A Novel Sustained-Release Formulation of Insulin with Dramatic Reduction in Initial Rapid Release," Journal of Controlled Release, Elsevier Science Publishers, vol. 79, No. 1-3, Feb. 19, 2002, pp. 81-91, XP004340914.

Hiroaki O. et al., "Biodegradable Microspheres in Drug Delivery," Critical Reviews in Therapeutic Drug Carrier Systems, vol. 12, No. 1, 1995, pp. 1-99, XP000604141.

Okada H, "One- and Three-Month Release Injectable Microspheres of the LH-RH Superagonist Leuprorelin Acetate," Advanced Drug Delivery Reviews, vol. 28, 1997, pp. 43-70, XP001040332.

Niwa T et al., "Preparations of Biodegradable Nanospheres of Water-Soluble and Insoluble Drugs With D, L-Lactide/Glycolide Copolymer by a Novel Spontaneous Emulsification Solvent Diffusion Method, and the Drug Release Behavior," Journal of Controlled Release, Elsevier Science Publishers B.V., vol. 25, No. 1 / 2, May 27, 1993, pp. 89-98, XP000361370.

Jeyanthi R et al., "Effect of Processing Parameters on the Properties of Peptide-Containing PLGA Microspheres," Journal of Microencapsulation, vol. 14, No. 2, Mar. 1, 1997, pp. 163-174, XP000643342.

Mohr D et al., "Gamma Irradiation for Terminal Sterilization of 17beta-Estradiol Loaded Poly-(d, l-lactide-co-glycolide) microparticles," Journal of Controlled Release, Elsevier Science Publishers, vol. 61, No. 1-2, Aug. 27, 1999, pp. 203-217, XP004362977.

Sanders L. M. et al., "Controlled Release of a Luteinizing Hormone-Releasing Hormone Analogue From Poly(D ,L-Lactide-Co-Glycolide) Microshperes," Journal of Pharmaceutical Sciences, American Pharmaceutical Association, vol. 73, N. 9, Sep. 1984, pp. 1294-1297, XP000942987.

(Continued)

Primary Examiner — Robert A Wax
Assistant Examiner — Hasan Ahmed
(74) Attorney, Agent, or Firm — Foley & Lardner LLP

(57) ABSTRACT

Present invention is to provide a sustained-release composition which contains a physiologically active substance in high content even when gelatin is not included, and suppresses its initial excessive release and, thus, can achieve a stable release rate over about one month. A sustained-release composition containing a lactic acid-glycolic acid polymer having a ratio or weight average molecular weight and number average molecular weight of about 1.90 or lower, or a salt thereof, and a physiologically active substance.

4 Claims, No Drawings

OTHER PUBLICATIONS

Office Action dated Nov. 6, 2009, in corresponding Korean Patent Application No. 2009-7017747,3 pages.

Kitchell et al., "Poly(lactic/glycolic acid) Biodegradable Drug-Polymer Matrix Systems," Methods in Enzymology, 1985, 112:436-448.

Amecke et al., "Synthetic Resorbable Polymers Based on Glycolide, Lactides, and Similar Monomers," Synthetic Resorbable Polymers, 1995, 977-1007.

Spicer et al., "Future possibilities in the prevention of breast cancer Luteinizing hormone-releasing hormone agonists," Breast Cancer Res., 2000, 2:264-267.

Wu, Xue Shen, "Synthesis and Properties of Biodegradable Lactic/Glycolic Acid Polymers," Encyclopedic Handbook of Biomaterials and Bioengineering, 1995, 2:1015-1054.

* cited by examiner

SUSTAINED-RELEASE COMPOSITION AND PROCESS FOR PRODUCING THE SAME

CROSS-REFERENCE TO RELATED APPLICATIONS

This application is a Divisional of U.S. application Ser. No. 10/479,516, which is the U.S. National Stage of PCT/JP02/06526, filed Jun. 28, 2002, which claims priority to Japanese Application No. 2001-199462, filed Jun. 29, 2001, and Japanese Application No. 2001-340980, filed Nov. 6, 2001. The entire contents of each of the aforementioned applications are incorporated herein by reference.

TECHNICAL FIELD

The present invention relates to a sustained-release preparation of a physiologically active substance and a process for producing the same.

BACKGROUND ART

In JP-A 60-100516, a sustained-release microcapsule of a water-soluble drug, which comprises a particle of an average diameter of 2 to 200 μm containing a water-soluble drug dispersed in a matrix comprising a lactic acid-glycolic acid copolymer having weight average molecular weight of about 5000 to 200000 and comprising about 100 to 50% by weight of lactic acid and about 0 to 50% by weight of glycolic acid, and which is prepared by a method of drying in water is disclosed.

In JP-A 62-201816, a sustained-release microcapsule characterized in that the viscosity of a W/O type emulsion upon preparation of a W/O/W type emulsion is adjusted to about 150 to 10000 cp, and a process for preparing the same are disclosed.

In JP-A 62-54760, there are disclosed a biodegradable polyoxycarboxylic ester which is a copolymer or a polymer having the content of water-soluble oxycarboxylic acid of less than 0.01 mole/100 g in terms of a monobasic acid and having a weight average molecular weight of about 2000 to 50000, and an injection sustained-release microcapsule containing the polymer.

In JP-A 61-28521, there are disclosed a lactic acid-glycolic acid copolymer which has weight average molecular weight of about 5000 to 30000, does not contain a catalyst, has the dispersibility (by a gel permeation chromatography method) of about 1.5 to 2 and comprises about 50 to 95% by weight of lactic acid and 50 to 5% by weight of glycolic acid, and a pharmaceutical containing the polymer as a base.

In JP-A 6-192068, there is disclosed a process for preparing a sustained-release microcapsule, which comprises heating a microcapsule at a temperature higher than the glass transition temperature of a polymer, at which respective particles of the microcapsule do not adhere to each other.

In JP-A 4-218528, there is disclosed a method for purifying biodegradable aliphatic polyester, which comprises dissolving a biodegradable aliphatic polyester containing a low-molecular weight polymer having a molecular weight of 1,000 or smaller in an organic solvent, adding water thereto to precipitate a polymeric substance, and removing low-molecular weight polymer having molecular weight of 1,000, and there is described that water is added at 50 to 150 (ratio by volume) relative to 100 of the organic solvent.

OBJECTS OF THE INVENTION

The present invention is to provide a sustained-release preparation which does not contain gelatin and contains a physiologically active substance in a large amount, and which can achieve a stable release rate over about one month by suppressing any initial excessive release of physiologically active substance.

SUMMARY OF THE INVENTION

In order to solve the aforementioned problem, the present inventors studied intensively and, as a result, found a sustained-release preparation which contains a physiologically active substance in a large amount without containing gelatin and which can suppress any initial excessive release of physiologically active substance to achieve a stable release rate over about one month, by preparing a polymer having a ratio of weight average molecular weight to number average molecular weight of PLGA as a base about 1.90 or lower, or by using a lactic acid-glycolic acid polymer having weight average molecular weight of about 11,600 to about 140,000 or a salt thereof, which resulted in completion of the present invention.

That is, the present invention provides:
(1) A sustained-release composition containing a lactic acid-glycolic acid polymer having a ratio of weight average molecular weight to number average molecular weight of about 1.90 or lower, or a salt thereof, and a physiologically active substance,
(2) the sustained-release composition described in the (1), wherein the physiologically active substance is a physiologically active peptide,
(3) the sustained-release composition described in the (2), wherein the physiologically active substance is an LH-RH derivative,
(4) the sustained-release composition described in the (1), wherein weight average molecular weight of a lactic acid-glycolic acid polymer is about 3,000 to about 100,000,
(5) the sustained-release composition described in the (4), wherein weight average molecular weight of a lactic acid-glycolic acid polymer is about 8,000 to about 15,000,
(6) the sustained-release composition described in the (1), wherein the ratio of the low molecular weight fraction of molecular weight of lactic acid-glycolic acid polymer of about 3,000 or smaller is about 9% or lower,
(7) the sustained-release composition described in the (6), wherein the ratio of the low molecular weight fraction of molecular weight of lactic acid-glycolic acid polymer of about 3,000 or smaller is about 3% to about 9%,
(8) the sustained-release composition described in the (1), wherein said polymer has a molar ratio of lactic acid to glycolic acid of from 100:0 to 40:60,
(9) the sustained-release composition described in the (1), wherein said polymer has a molar ratio of lactic acid to glycolic acid of from 70:30 to 80:20,
(10) the sustained-release composition described in the (3), wherein the LH-RH derivative is a peptide represented by the formula:

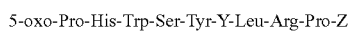
5-oxo-Pro-His-Trp-Ser-Tyr-Y-Leu-Arg-Pro-Z wherein Y denotes DLeu, DAla, DTrp, DSer(tBu), D2Nal or DHis(ImBzl), and Z denotes HN—$C_2H_5$ or Gly-$NH_2$, or a salt thereof,
(11) the sustained-release composition described in the (3), wherein the LH-RH derivative is a peptide represented by the formula:

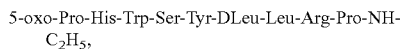
5-oxo-Pro-His-Trp-Ser-Tyr-DLeu-Leu-Arg-Pro-NH-$C_2H_5$, or acetate thereof,

(12) the sustained-release composition described in the (3), wherein the LH-RH derivative or a salt thereof is contained at about 5% (w/w) to about 24% (w/w) in the sustained-release composition,
(13) the sustained-release composition described in the (1), wherein the physiologically active substance or a salt thereof is slightly water-soluble or water-soluble,
(14) the sustained-release composition described in the (1), which is for injection,
(15) the sustained-release composition described in the (1), which releases a physiologically active substance or a salt thereof over at least two weeks,
(16) the sustained-release composition described in the (1), which does not contain a drug retaining substance,
(17) the sustained-release composition described in the (1), which does not contain gelatin,
(18) a process for producing the sustained-release composition as defined in the (1), which comprises removing a solvent from a mixed solution containing a physiologically active substance or a salt thereof and a lactic acid-glycolic acid polymer having a ratio of weight average molecular weight to number average molecular weight of about 1.90 or lower, or a salt thereof,
(19) the process described in the (18), which comprises mixing and dispersing a physiologically active substance or a salt thereof in a solution, in an organic solvent, containing a lactic acid-glycolic acid polymer having a ratio of weight average molecular weight to number average molecular weight of about 1.90 or lower, or a salt thereof, and removing the organic solvent,
(20) the process described in the (19), wherein the physiologically active substance or a salt thereof is used as an aqueous solution containing the physiologically active substance or a salt thereof,
(21) a pharmaceutical comprising the sustained-release composition as defined in the (1),
(22) an agent for preventing or treating prostate cancer, prostatomegaly, endometriosis, hysteromyoma, metrofibroma, precocious puberty, dysmenorrhea and breast cancer, or a contraceptive, which comprises the sustained-release composition as defined in the (3),
(23) an agent for preventing recurrence of breast cancer after the operation for premenopausal breast cancer, which comprises the sustained-release composition as defined in the (3),
(24) a method for preventing or treating prostate cancer, prostatomegaly, endometriosis, hysteromyoma, metrofibroma, precocious puberty and dysmenorrhea, or a contraceptive, which comprises administering to a mammal an effective dose of the sustained-release composition as defined in the (3),
(25) a method for preventing recurrence of breast cancer after the operation for premenopausal breast cancer, which comprises administering to a mammal an effective dose of the sustained-release composition as defined in the (3),
(26) a process for producing a lactic acid-glycolic acid polymer having a weight average molecular weight of about 8,000 to about 15,000 and having a ratio of weight average molecular weight to number average molecular weight of about 1.90 or lower, or a salt thereof, which comprises adding water to an organic solvent containing a lactic acid-glycolic acid polymer having weight average molecular weight of about 5,000 to about 15,000 at a ratio of less than about 5 to 50 (ratio by volume) relative to 100 of the organic solvent,
(27) the process for producing a polymer described in the (26), wherein the organic solvent is hydrophilic,
(28) the process for producing a polymer described in the (27), wherein the hydrophilic organic solvent is acetone,
(29) the process for producing a polymer described in the (26), wherein the ratio of water relative to 100 of the organic solvent is about 10 to about 45 (ratio by volume),
(30) the process for producing a polymer described in the (26), wherein the ratio of water relative to 100 of the organic solvent is about 40 (ratio by volume),
(31) a lactic acid-glycolic acid polymer having weight average molecular weight of about 8,000 to about 15,000 and having a ratio of weight average molecular weight to number average molecular weight of about 1.90 or lower, or a salt thereof,
(32) use of lactic acid-glycolic acid polymer or salt thereof described in the (31) for producing the sustained-release composition which does not include gelatin,
(33) a microsphere containing a lactic acid-glycolic acid polymer having weight average molecular weight of about 11,600 to about 14,000 or a salt thereof, and a LH-RH derivative or a salt thereof, and not containing gelatin,
(34) the microsphere described in the (33), wherein the LH-RH derivative or a salt thereof is a peptide represented by the formula:

5-oxo-Pro-His-Trp-Ser-Tyr-Y-Leu-Arg-Pro-Z wherein Y denotes DLeu, DAla, DTrp, DSer(tBu), D2Nal or DHis(ImBzl), and Z denotes HH, $C_2H_5$ or Gly-$NH_2$, or a salt thereof,
(35) the microsphere described in the (33), wherein the LH-RH derivative or a salt thereof is a peptide represented by the formula:

5-oxo-Pro-His-Trp-Ser-Tyr-DLeu-Leu-Arg-Pro-NH-$C_2H_5$, or acetate thereof,
(36) the microsphere described in the (33), wherein the LH-RH derivative or a salt thereof is contained at about 5% (w/w) to about 24% (w/w),
(37) the microsphere described in the (33), which is a microcapsule,
(38) the microsphere described in the (33), wherein the LH-RH derivative or a salt thereof is released during at least more than 2 weeks,
(39) an agent for preventing or treating prostate cancer, prostatomegaly, endometriosis, hysteromyoma, metrofibroma, precocious puberty and dysmenorrhea, or a contraceptive, which comprises the microsphere described in the (33),
(40) an agent for preventing recurrence of breast cancer after the operation for premenopausal breast cancer, which comprises the microsphere described in the (33),
(41) a method for preventing or treating prostate cancer, prostatomegaly, endometriosis, hysteromyoma, metrofibroma, precocious puberty and dysmenorrhea, or a contraceptive, which comprises administering to a mammal an effective dose of the microsphere described in the (33),
(42) a method for preventing recurrence of breast cancer after the operation for premenopausal breast cancer, which comprises administering to a mammal an effective dose of the microsphere described in the (33).

DETAILED DESCRIPTION OF THE INVENTION

The physiologically active substance used in the present invention is not particularly limited as long as it is pharmaceutically useful, and a non-peptide compound or peptide compound. Examples of a suitable non-peptide compound include an agonist, an antagonist, and a compound having the enzyme inhibiting activity. In addition, as the peptide compound, for example, a physiologically active peptide is preferable. Physiologically active peptides having a molecular weight of about 3000 to about 40,000, preferably about 4000 to about 30,000, more preferably about 5000 to about 200,000 are suitable.

Examples of the physiologically active peptide include luteinizing hormone-releasing hormone (LH-RH), insulin, somatostatin, somatotropin, growth hormone-releasing hormone (GH-RH), prolactin, erythropoietin, adrenal cortical hormone, melanocyte-stimulating hormone, thyroid hormone-releasing hormone, thyroid-stimulating hormone, luteinizing hormone, follicle-stimulating hormone, vasopressin, oxytocin, calcitonin, gastrin, secretin, pancreozymin, cholecystokinin, angiotensin, human placental lactogen, human chorionic gonadotropin, enkephalin, endorphin, kyotrophin, tuftsin, thymopoietin, thymosin, thymotimurin, thymus humoran factor, blood thymus factor, tumor necrosis factor, colony-inducing factor, motilin, dynorphin, bombesin, neurotensin, cerulein, bradykinin, atrial natriuretic excretion-increasing factor, nerve growth factor, cell growth stimulator, neurotrophic factor, peptides having the endothelin antagonistic activity and derivatives, fragments thereof and derivatives of the fragments.

The physiologically active substance used in the present invention may be itself or maybe a pharmacologically salt thereof.

When the physiologically active substance has a basic group such as an amino group, examples of such salts include salts with inorganic acids (also referred to as inorganic free acid) (for example, carbonic acid, bicarbonic acid, hydrochloric acid, sulfuric acid, nitric acid, boric acid and the like), and organic acids (also referred to as organic free acid) (for example, succinic acid, acetic acid, propionic acid, trifluoroacetic acid and the like), when the physiologically active substance has an acidic group such as a carboxyl group and the like, examples of such the salt include salts with inorganic base (also referred to as inorganic free base) (for example, alkali metal such as sodium, potassium and the like, alkaline earth metal such as calcium, magnesium and the like), and organic bases (also referred to as organic free base) (for example, organic amines such as triethylamine and the like, basic amino acids such as arginine and the like). In addition, the physiologically active peptide may form a metal complex compound (for example, copper complex, zinc complex and the like).

Preferable examples of the physiologically active peptide include LH-RH derivatives or salts thereof which are effective for hormone dependent diseases, in particular, sex hormone dependent cancers (for example, prostate cancer, uterine cancer, breast cancer, pituitary gland tumor and the like), sex hormone dependent disease such as prostatomegaly, endometriosis, hysteromyoma, precocious puberty, dysmenorrhea, amenorrhea, premenstrual syndrome, multilocular ovary syndrome and the like, contraception (or, when the rebound activity after cease of administration is utilized, infertility), prevention of recurrence of breast cancer after the operation for premenopausal breast cancer. Further, examples include LH-RH derivatives or salts thereof effective for benign or malignant tumors which are sex hormone independent but LH-RH sensitive.

Specific examples of the LH-RH derivatives or salts thereof include peptides described in Treatment with GnRH analogs: Controversies and perspectives (The parthenon Publishing Group Ltd.) published in 1996, JP-A 3-503165, JP-A 3-101695, JP-A 7-97334 and JP-A 8-259460.

Examples of the LH-RH derivatives include LH-RH agonists and LH-RH antagonists. As the LH-RH antagonists, for example, a physiologically active peptide represented by the general formula [I]:

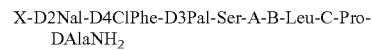

[wherein X denotes N(4H$_2$-furoyl)Gly or NAc, A denotes a residue selected from NHeTyr, Tyr, Aph(Atz), and NMeAph (Atz), B denotes a residue selected from DLys(Nic), DCit, DLis(AzaglyNic), DLis(AzaglyFur) DhArg(Et$_2$), DAph (Atz) and DhCi, and C denotes Lys(Nisp), Arg or hArg(Et$_2$)], and a salt thereof are used.

As the LH-RH agonist, for example, a physiologically active peptide represented by the general formula [II]:

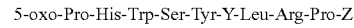

[wherein Y denotes a residue selected from DLeu, DAla, DTrp, DSer(tBu), D2Nal and DHis(ImBzl), and Z denotes NH-C$_2$H$_5$ or Gly-NH$_2$]
or a salt thereof is used. In particular, a peptide wherein Y is DLeu and Z is NH-C$_2$H$_5$ (that is, Peptide A represented by 5-oxo-Pro-His-Trp-Ser-Tyr-DLeu-Leu-Arg-Pro-NH-C$_2$H$_5$; Leuprorelin) or a salt thereof (for example, acetate) is suitable.

These peptides can be prepared by the methods described in the aforementioned publications or patent publications or similar methods.

Abbreviations used in the present specification have the following meanings:

| Abbreviation | Name |
| --- | --- |
| N(4H$_2$-furoyl)Gly: | N-tetrahydrofuroylglycine residue |
| NAc | N-acetyl group |
| N2Nal | D-3-(2-naphthyl)alanine residue |
| D4ClPhe | D-3-(4-chloro)phenylalanine residue |
| D3Pal | D-3-(3-pyridyl)alanine residue |
| NMeTyr | N-methyl tyrosine residue |
| Aph(Atz) | N-[5'-(3'-amino-1'H-1',2',4'-triazolyl)] phenylalanine residue |
| NMeAph(Atz) | N-methyl-[5'-(3'-amino-1'H-1',2',4'-triazolyl)]phenylalanine residue |
| DLys(Nic) | D-(e-N-nicotinoyl)lysine residue |
| Dcit | D-citrulline residue |
| DLys(AzaglyNic) | D-(azaglycylnicotinoyl)lysine residue |
| DLys(AzaglyFur) | D-(azaglycylfuranyl)lysine residue |
| DhArg(Et$_2$) | D-(N,N'-diethyl)homoarginine residue |
| DAph(Atz) | D-N-[5'-(3'-amino-1'H-1',2',4'-triazolyl)]phenylalanine residue |
| DhCi | D-homocitrulline residue |
| Lys(Nisp) | (e-N-isopropyl)lysine residue |
| hArg(Et$_2$) | (N,N'-diethyl)homoarginine residue |

Regarding other acids, abbreviation is expressed based on abbreviations according to IUPAC-IUB Commission on Biochemical Nomenclature (European Journal of Biochemistry, Vol. 138, pp 9-37 (1984)) or the conventional abbreviations in the art. In addition, when an amino acid can have an optical isomer, it denotes L-amino acid unless indicated otherwise.

As a lactic acid-glycolic acid polymer used in the present invention, a lactic acid-glycolic acid polymer having a ratio of weight average molecular weight of the lactic acid-glycolic acid polymer to number average molecular weight of the lactic acid-glycolic acid polymer of about 1.90 or lower is preferably used.

A lactic acid-glycolic acid copolymer may be a salt. Examples of the salt include salts with inorganic bases (for example, alkali metal such as sodium, potassium and the like, and alkaline earth metal such as calcium, magnesium and the like) or organic bases (for example, organic amines such as triethylamine and the like, and basic amino acids such as arginine and the like), salts with transition metals (for example, zinc, iron, copper and the like), and complex salts.

A constitutional molar ratio of the lactic acid-glycolic acid polymer is preferably about 100/0 to about 40/60, more preferably about 70/30 to about 80/20.

A optical isomer ratio of lactic acid which is one of minimum repeating units of the "lactic acid-glycolic acid polymer" is preferably in a range of D-isomer/L-isomer (mole/mole %) of about 75/25 to about 25/75. In particular, the D-isomer/L-isomer (mole/mole %) in a range of about 60/40 to about 30/70 is frequently used.

A weight average molecular weight of the "lactic acid-glycolic acid polymer" is usually about 3,000 to about 100,000, preferably about 3,000 to about 50,000, particularly preferably about 8,000 to about 15,000.

A ratio of a low molecular weight fraction, having molecular weight of about 3,000 or smaller, of the "lactic acid-glycolic acid polymer" is preferably about 9% or lower, more preferably about 3% to 9% or lower.

In addition, a lactic acid-glycolic acid polymer in the present invention has a ratio of weight average molecular weight of the lactic acid-glycolic acid polymer to number average molecular weight of the lactic acid-glycolic acid polymer of about 1.90 or lower, preferably about 1.40 to about 1.90, more preferably about 1.45 to about 1.80.

Further, preferable examples include:
(1) a lactic acid-glycolic acid polymer having a weight average molecular weight of about 3,000 to 100,000 and having a ratio of weight average molecular weight of a lactic acid-glycolic acid polymer to number average molecular weight of a lactic acid-glycolic acid polymer of about 1.90 or lower,
(2) a lactic acid-glycolic acid polymer having a weight average molecular weight of about 3,000 to 50,000 and having a ratio of weight average molecular weight of a lactic acid-glycolic acid polymer to number average molecular weight of a lactic acid-glycolic acid polymer of about 1.90 or lower,
(3) a lactic acid-glycolic acid polymer having a weight average molecular weight of about 8,000 to 15,000 and having a ratio of weight average molecular weight of a lactic acid-glycolic acid polymer to number average molecular weight of a lactic acid-glycolic acid polymer of about 1.90 or lower,
(4) a sustained-release composition described in the (1) to (3), wherein a ratio of a low molecular weight fraction, having molecular weight of about 3,000 or smaller, of a lactic acid-glycolic acid polymer is about 9% or lower, and
(5) a sustained-release composition described in the (1) to (3), wherein a ratio of a low molecular weight fraction, having molecular weight of about 3,000 or smaller, of a lactic acid-glycolic acid polymer is about 3% to about 9%.

More preferable examples include:
(6) a lactic acid-glycolic acid polymer having weight average molecular weight of about 3,000 to 100,000 and having a ratio of weight average molecular weight of a lactic acid-glycolic acid polymer to number average molecular weight of a lactic acid-glycolic acid polymer of about 1.40 to about 1.90,
(7) a lactic acid-glycolic acid polymer having a weight average molecular weight of about 3,000 to 50,000 and having a ratio of weight average molecular weight of a lactic acid-glycolic acid polymer to number average molecular weight of a lactic acid-glycolic acid polymer of about 1.40 to about 1.90,
(8) a lactic acid-glycolic acid polymer having weight average molecular weight of about 8,000 to 15,000 and having a ratio of weight average molecular weight of a lactic acid-glycolic acid polymer to number average molecular weight of a lactic acid-glycolic acid polymer of about 1.40 to about 1.90,
(9) a sustained-release composition described in the (6) to (8), wherein a ratio of a low molecular weight fraction, having molecular weight of about 3,000 or smaller, of a lactic acid-glycolic acid polymer is about 9% or lower, and
(10) a sustained-release composition described in the (6) to (8), wherein a ratio of a low molecular weight fraction, having molecular weight of about 3,000 or smaller, of a lactic acid-glycolic acid polymer is about 3% to about 9%.

Most preferable examples include:
(11) a lactic acid-glycolic acid polymer having weight average molecular weight of about 3,000 to 100,000 and having a ratio of weight average molecular weight of a lactic acid-glycolic acid polymer to number average molecular weight of a lactic acid-glycolic acid polymer of about 1.45 to about 1.80,
(12) a lactic acid-glycolic acid polymer having weight average molecular weight of about 3,000 to 50,000 and having a ratio of weight average molecular weight of a lactic acid-glycolic acid polymer to number average molecular weight of a lactic acid-glycolic acid polymer of about 1.45 to about 1.80,
(13) a lactic acid-glycolic acid polymer having weight average molecular weight of about 3,000 to 15,000 and having a ratio of weight average molecular weight of a lactic acid-glycolic acid polymer to number average molecular weight of a lactic acid-glycolic acid polymer of about 1.45 to about 1.80,
(14) a sustained-release composition described in the (11) to (13), wherein a ratio of a low molecular weight fraction, having molecular weight of about 3,000 or smaller, of a lactic acid-glycolic acid polymer is about 9% or lower, and
(15) a sustained-release composition described in the (11) to (13), wherein a ratio of a low molecular weight fraction, having molecular weight of about 3,000 or smaller, of a lactic acid-glycolic acid polymer is about 3% to about 9%.

Furthermore, a lactic acid-glycolic acid polymer having weight average molecular weight of about 11,600 to about 14,000 or a salt thereof may be used.

Weight average molecular weight and number average molecular weight in the present specification refer to molecular weight in terms of polystyrene measured by gel permeation chromatography (GPC) using as a standard substance ten kinds of monodisperse polystyrene having (GPC1) weight average molecular weight of 397000, 189000, 98900, 37200, 17100, 9490, 5870, 2500, 1050 and 495.

Further, the amount of a low molecular weight fraction of the polymer having a molecular weight of about 3,000 or smaller denotes the amount of a fraction having a molecular weight of about 3,000 or smaller within a weight average molecular weight distribution pattern obtained in the aforementioned GPC measurement. More specifically, the amount of the area under the curve of a part corresponding to a molecular weight of about 3,000 or smaller relative to the area under the curve of the calculated weight average molecular weight distribution pattern is calculated. Measurement is performed by using a series of high speed GPC apparatus (manufactured by Toso, HLC-8120GPC, a detection method is by differential refractive index), TSKguardcolumn Super H-L (4.6 mmi.d.×35 mm), TSKgel SuperH4000(6 mmi.d.×150 mm)×2, and TSKgel SuperH2000(6 mmi,d,×150 mm) (All columns are manufactured by Toso) and THF as a mobile phase at a flow rate of 0.6 ml/min.

When the reaction between a lactic acid-glycolic acid polymer and a physiologically active substance is an ionic interaction, the main interaction is between the physiologically active substance and terminal carboxylic acid of a lactic acid-glycolic acid polymer. When the low molecular weight fraction is contained in a large amount, a physiologically active substance readily interacts with a lactic acid-glycolic acid polymer of a low molecular weight having high reactivity. In a sustained-release injection agent, a physiologically active substance involved in leakage upon preparation and initial release is mainly a physiologically active substance interacted with this lactic acid-glycolic acid polymer of a low molecular weight fraction. In order to increase the content of the physiologically active substance and suppress the amount of its initial release, it is necessary that a ratio of this lactic acid-glycolic acid polymer of a low molecular weight fraction is reduced below a certain level, and the ratio of weight average molecular weight to number average molecular weight is reduced below a certain level. For this reason, for example, in order to obtain a lactic acid-glycolic acid polymer for an one month-type sustained release preparation, a lactic acid-glycolic acid polymer is preferable, such a lactic acid-glycolic acid is preferable that the aforementioned weight average molecular weight is about 8,000 to about 15,000, a ratio of weight average molecular weight to number average molecular weight is about 1.90 or lower, preferably about 1.40 to about 1.90, more preferably about 1.45 to about 1.80, and the amount of a low molecular weight fraction having a weight average molecular weight of 3,000 or smaller is about 9% or lower, preferably about 3% to about 9%.

The "lactic acid-glycolic acid polymer" can be prepared by dehydration polycondensation without a catalyst from lactic acid and glycolic acid (JP-A 61-28521) or ring-opening polymerization from lactide and a cyclic diester compound such as glycolide and the like (Encyclopedic Handbook of Biomaterials and Bioengineering Part A: Materials, Volume 2, Marcel Dekker, Inc, 1995).

A lactic acid-glycolic acid polymer obtained by dehydration polycondensation without a catalyst from lactic acid and glycolic acid generally has a large amount of low molecular weight fraction, and has a ratio of weight average molecular weight to number average molecular weight of about 2 or higher. The weight average molecular weight of a lactic acid-glycolic acid copolymer used in the present specification is about 5,000 to about 15,000. The amount of the low molecular weight fraction having a molecular weight of about 3,000 or smaller can vary depending on weight average molecular weight and, when weight average molecular weight is about 10,000, the amount of low molecular weight fraction having molecular weight of about 3,000 or smaller is about 10% or higher.

The resulting lactic acid-glycolic acid polymer can be purified by using an organic solvent to obtain an end polymer.

Examples of an organic solvent used in the present invention include preferably a hydrophilic or a readily water-soluble organic solvent such as, for example, acetone, tetrahydrofuran, dioxane, dimethylformamide and dimethyl sulfoxide and, inter alia, acetone is preferably used.

The amount of water and organic solvent used in the present invention to be added is not particularly limited. However, when the amount of water is too large, reduction of the low molecular weight fraction is insufficient and, thus, it is difficult to obtain an end polymer. On the other hand, when the amount of water is too small, the polymer becomes difficult to precipitate and, therefore, recovery is deteriorated and only a polymer having a higher molecular weight than the desired molecular weight is recovered. Usually, the amount of water relative to 100 of an organic solvent is about 5 to 50, preferably about 10 to about 45, more preferably about 24 to about 40, particularly preferably about 40. For example, 10 g of a lactic acid-glycolic acid polymer is dissolved in 100 mL of acetone which is an organic solvent, 40 mL of purified water is gradually added thereto while stirring by a suitable method, to precipitate an end polymer, which can be dried by a suitable method. When an end polymer can not be obtained by a single dissolution and precipitation step, this procedure may be repeated.

In the sustained-release preparation of the present invention, a base is preferably a lactic acid-glycolic acid polymer having a ratio of weight average molecular weight to number average molecular weight of about 1.90 or lower, or a salt thereof, or a lactic acid-glycolic acid polymer having weight average molecular weight of about 11,600 to about 14,000 or a salt thereof. A constitutional molar ratio of lactic acid and glycolic acid is preferably 100/0 to 40/60. A physiologically active substance is preferably a LH-RH derivative and particularly preferably a LH-RH derivative is the peptide represented by the formula:

$$\text{5-oxo-Pro-His-Trp-Ser-Tyr-DLeu-Leu-Arg-Pro-NH-C}_2\text{H}_5$$

or acetate thereof. The content of a LH-RH derivative or a salt thereof is preferably about 5% (w/w) to about 24% (w/w). Further, preferable is such a sustained-release preparation that does not contain gelatin and releases a physiologically active substance or a salt thereof over at least two weeks.

A Method of Preparing a Microcapsule

The thus obtained lactic acid-glycolic acid polymer can be used as a base for preparing a sustained-release preparation. A method of preparing a sustained-release composition, for example, a microcapsule containing a physiologically active substance or a salt thereof, and a lactic acid-glycolic acid polymer or a salt thereof of the present invention is exemplified.

(I) A method of Drying in Water
(i) O/W Method

In the present method, first, a solution of a lactic acid-glycolic acid polymer or a salt thereof in an organic solvent is prepared. It is preferable that an organic solvent used for preparing a sustained-release preparation of the present invention has a boiling point of 120° C. or lower.

As the organic solvent, for example, halogenated hydrocarbon (for example, dichloromethane, chloroform, dichloroethane, trichloroethane, carbon tetrachloride and the like), ethers (for example, ethyl ether, isopropyl ether and the like), fatty acid ester (for example, ethyl acetate, butyl acetate and the like), aromatic hydrocarbon (for example, benzene, toluene, xylene and the like), alcohols (for example, ethanol, methanol and the like), and acetonitrile are used, and a solvent of the mixture of them is used. As an organic solvent for a lactic acid-glycolic acid polymer or a salt thereof, inter alia, dichloromethane is preferable.

The concentration of lactic acid-glycolic acid polymer in solution in an organic solvent can vary depending on the molecular weight of a lactic acid-glycolic acid polymer and the type of organic solvent. For example, when dichloromethane is used as an organic solvent, the concentration is selected generally from about 0.5 to about 70% by weight, more preferably about 1 to about 60% by weight, particularly preferably about 2 to about 50% by weight.

A physiologically active substance or a salt thereof is added to, and dissolved or dispersed in the thus obtained solution of a lactic acid-glycolic acid polymer in an organic solvent. Then, the resulting solution in an organic solvent containing a composition comprising a physiologically active substance or a salt thereof and a lactic acid-glycolic acid polymer or a salt thereof is added to an aqueous phase to form an O (oily phase)/W (aqueous phase) emulsion, a solvent in an oily phase is volatilized or diffused in an aqueous phase to prepare a microcapsule. Upon this, a volume of an aqueous phase is selected generally from about 1 to about 10,000-fold, more preferably about 5 to 50,000-fold, particularly preferably about 10 to 2,000-fold an oily phase volume.

An emulsifier may be added to an aqueous phase besides the aforementioned components. Any emulsifier may be used as long as it can generally form a stable O/W emulsion. Specifically, for example, anionic surfactants (sodium oleate, sodium stearate, sodium laurylsulfate and the like), nonionic surfactants (polyoxyethylene sorbitan fatty acid esters (Tween 80, Tween 60, manufactured by Atlas Powder), polyoxyethylene castor oil derivative (HCO-60, HCO-50, manufactured by Nikko Chemical), polyvinyl pyrrolidone, polyvinyl alcohol, carboxymethylcellulose, lecithin, gelatin and hyaluronic acid are used. These may be used alone or in combination of some of them. The concentration upon use is preferably in a range of about 0.0001 to 10% by weight, more preferably in a range of about 0.001 to 5% by weight.

An osmotic pressure regulating agent may be added to an aqueous phase besides the aforementioned components. Any osmotic pressure regulating agent may be used as long as it produces osmotic pressure when formulated into an aqueous solution.

Examples of the osmotic pressure regulating agent include polyhydric alcohols, monohydric alcohols, monosaccharides, disaccharides, oligosaccharide and amino acids or derivatives thereof.

As the polyhydric alcohols, for example, trihydric alcohols such as glycerin and the like, pentahydric alcohols such as arabitol, xylitol, adonitol and the like, and hexahydric alcohols such as mannitol, sorbitol, dulcitol and the like are used. Inter alia, hexahydric alcohols are preferable, in particular, mannitol is suitable.

Examples of the monohydric alcohols include methanol, ethanol and isopropyl alcohol and, inter alia, ethanol is preferable.

As the monosaccharides, for example, pentoses such as arabinose, xylose, ribose, 2-deoxyribose and the like, and hexoses such as glucose, fructose, galactose, mannose, sorbose, rhamnose, fucose and the like are used and, among them, hexoses are preferable.

As the oligosaccharides, for example, trisaccharides such as maltotriose, raffinose and the like, and tetrasaccharides such as stachyose and the like are used and, among them, trisaccharides are preferable.

As the derivatives of monosaccharides, disaccharides and oligosaccharide, for example, glucosamine, galactosamine, glucuronic acid and galacturonic acid are used.

As the amino acids, any L-amino acids can be used and examples thereof include glycine, leucine and arginine. Among them, L-arginine is preferable.

These osmotic regulating agents may be used alone or in combination.

These osmotic regulating agents are used at the concentration such that osmotic pressure of an external aqueous phase is about 1/50 to about 5-fold, preferably about 1/25 to about 3-fold osmotic pressure of a physiological saline solution. When mannitol is used as an osmotic pressure regulating agent, its concentration is preferably 0.5% to 1.5%.

As a method of removing organic solvent, the method known per se or a similar method is used. Examples of the method include a method of evaporating an organic solvent at a normal pressure or by reducing pressure to reduced pressure gradually while stirring with a propeller type stirrer, a magnetic stirrer or an ultrasound generating apparatus, a method of evaporating an organic solvent while the vacuum degree is regulated using a rotary evaporator, and a method of gradually removing an organic solvent using a dialysis membrane.

The thus obtained microcapsule is centrifuged or filtered to recover a free physiologically active substance or a salt thereof, a drug retaining substance and an emulsifier which are attached to the surface of a microcapsule, are washed with distilled water several times, and dispersed again in distilled water, which is lyophilized.

Since a microcapsule of the present invention uses as a base a lactic acid-glycolic acid polymer having a ratio of weight average molecular weight to number average molecular weight of 1.90 or lower, or a salt thereof, or a lactic acid-glycolic acid polymer having weight average molecular weight of about 11,600 to about 14,000 or a salt thereof, the microcapsule can contain a drug in high content and, thus, it is not necessary that the microcapsule contains a drug retaining substance such as gelatin and a thickening agent.

These polymers can be used preferably for manufacturing a sustained-release composition which releases a drug over at least two weeks.

During the preparation step, an aggregation-preventing agent may be added in order to prevent aggregation of particles. As the aggregation-preventing agent, for example, a water soluble polysaccharide such as mannitol, lactose, glucose and starches (for example, corn starch and the like), an amino acid such as glycine, and a protein such as fibrin and collagen are used. Among them, mannitol is suitable.

After lyophilization, if necessary, water and an organic solvent in the microcapsule may be removed by warming within conditions under which microcapsules are not fused. Preferably, warming is performed at a temperature around or slightly higher than an intermediate glass transition temperature of a microcapsule obtained by a differential scanning calorimeter under the conditions of a temperature increasing rate of 10 to 20° C. per min. More preferably, warming is performed at a temperature around the intermediate glass transition temperature of a microcapsule or in the temperature range from the intermediate glass transition temperature of a microcapsule to a temperature higher by about 30° C. than the intermediate glass transition temperature thereof. Preferably, warming is performed in the range of a temperature from around the intermediate glass transition temperature of a microcapsule to higher by 10° C. than the intermediate glass transition temperature thereof, more preferably in the range of a temperature from around the intermediate glass transition temperature to higher by 5° C. than the intermediate glass transition temperature.

Warming time can vary depending on the amount of microcapsule and is generally about 12 hours to 168 hours, preferably about 24 hours to 120 hours, particularly preferably about 48 hours to 96 hours after the temperature of the microcapsule itself reaches a prescribed temperature.

The warming method is not particularly limited as long as the aggregation of microcapsules is uniformly warmed by the method.

As a method of warming and drying, for example, a method of warming and drying in a thermostatic chamber, a fluidizing chamber, a moving chamber or a kiln, and a method of warming and drying with a microwave are used. Among them, a method of warming and drying in a thermostatic chamber is preferable.

(ii) W/O/W Method

First, a solution of a lactic acid-glycolic acid polymer or a salt thereof in an organic solvent is prepared, and the thus obtained organic solvent solution is referred to as an oily phase. The method of preparation is the same as that described in section (I)(i) above. The concentration of lactic acid-glycolic acid polymer in an organic solvent can vary depending on the molecular weight of lactic acid-glycolic acid polymer and type of organic solvent and, for example, when dichloromethane is used as an organic solvent, the concentration is selected from generally about 0.5 to about 70% by weight, more preferably about 1 to about 60% by weight, particularly preferably about 2 to about 50% by weight.

Next, a solution or a dispersion of a physiologically active substance or a salt thereof [the solvent is water or a mixture of water and alcohols (for example, methanol, ethanol and the like)] is prepared.

The concentration of physiologically active substance or a salt thereof to be added is generally 0.001 mg/ml to 10 g/ml, more preferably 0.1 mg/ml to 5 g/ml, more preferably 10 mg/ml to 3 g/ml.

When the above-described physiologically active substance has a basic group such as amino group, salts of physiologically active substance include a salt with inorganic acid (also referred to as inorganic free acid) (for example, carbonic acid, acid carbonate, hydrochloric acid, sulfuric acid, nitric acid, boric acid etc.), organic acid (also referred to as organic free acid) (for example, succinic acid, acetic acid, propionic acid, trifluoracetic acid etc.).

When a physiologically active substance has a acidic group such as carboxyl group, salts of physiologically active substance include a salt with inorganic base (also referred to as inorganic free base) (for example, alkali metals such as sodium, potassium, alkali earth metals such as calcium, magnesium, etc.), organic base (also referred to as organic free base) (for example, organic amines such as triethylamine, basic amino acids such as arginine, etc.). Further, physiologically active peptides may form a metal complex compound (for example, copper complex, zinc complex etc.). When a physiologically active substance is a LHRH derivative, acetic acid is particularly preferably added.

As a solubilizing agent and a stabilizing agent, known ones may be used. In order to dissolve or disperse a physiologically active substance or an additive, heating, shaking and stirring may be performed to such an extent that the activity is not lost, and thus obtained aqueous solution is referred to as an inner aqueous phase.

The thus obtained inner aqueous phase and oily phase are emulsified by known methods such as a homogenization and ultrasound to form a W/O emulsion.

The volume of oily phase to be mixed is about 1 to about 1000-fold, preferably 2 to 100-fold, more preferably about 3 to 10-fold relative to the volume of the inner aqueous phase.

The range of the viscosity of the resulting W/O emulsion is generally about 10 to 10,000 cp, preferably about 100 to 5,000 cp, particularly preferably about 500 to 2,000 cp at about 12 to 25° C.

Then the resulting W/O emulsion comprising a physiologically active substance or a salt thereof and a lactic acid-glycolic acid polymer or a salt thereof is added to an aqueous phase to form a W (inner aqueous phase)/O (oily phase)/W (external aqueous phase), a solvent in an oily phase is volatilized or diffused into an external aqueous phase to prepare a microcapsule. Upon this, a volume of an external aqueous phase is selected from generally about 1-fold to about 10,000-fold, more preferably about 5-fold to about 50,000-fold, particularly preferably about 10-fold to about 2,000-fold a volume of an oily phase.

An emulsifier and an osmotic pressure regulating agent which may be added to the aqueous phase besides the aforementioned components, and the methods of preparation thereafter are the same as those described in section (I)(i) above.

(II) Phase Separating Method

When a microcapsule is prepared by the present method, a coacervating agent is gradually added to an organic solvent solution containing a physiologically active substance or a salt thereof and a lactic acid-glycolic acid polymer or a salt thereof described in a method of drying in water in the (I) while stirring, to precipitate and solidify a microcapsule. The volume of the coacervating agent may be from about 0.01 to 1,000-fold, preferably about 0.05 to 500-fold, particularly preferably about 0.1 to 200-fold of the volume of the oily phase.

The coacervating agent is not particularly limited as long as it is a polymer series, mineral oil series or plant oil series compound which is compatible with an organic solvent, and does not dissolve the complex of the physiologically active substance or a salt thereof and the lactic acid-glycolic acid polymer of a salt thereof. Specifically, for example, silicone oil, sesame oil, soybean oil, corn oil, cottonseed oil, coconut oil, linseed oil, mineral oil, n-hexane or n-heptane may be used. These may be used by mixing 2 or more of them.

The thus obtained microcapsule is recovered, washed repeatedly with heptane or the like to remove the coacervating agent from the composition comprising a physiologically active substance or a salt thereof and a lactic acid-glycolic acid polymer or a salt thereof, which is then dried under reduced pressure. Alternatively, washing is performed in the same manner as that described as a method of drying in water in section (I)(i) above, which is lyophilized and further warmed and dried.

(III) Spraying Drying Method

When a microcapsule is prepared by the present method, an organic solvent solution containing a physiologically active substance or a salt thereof and a lactic acid-glycolic acid polymer or a salt thereof described in a method of drying in water in section (I) is sprayed in a drying chamber of a spray dryer using a nozzle, and an organic solvent in finely-divided droplets is volatilized in an extremely short time to prepare a microcapsule. Examples of the nozzle include to fluid nozzle type, pressure nozzle type, rotation disc type. Thereafter, if necessary, the microcapsule may be washed, lyophilized and further warmed and dried by the same method as that described in a method of drying in water in section (I).

As a dosage form other than the aforementioned microcapsule, an organic solvent solution containing a physiologically active substance or a salt thereof and a lactic acid-glycolic acid polymer or a salt thereof described in a method of drying in water in a method of preparing a microcapsule (I) is dried by evaporating an organic solvent and water while the degree of vacuum is regulated using, for example, a rotary evaporator, which may be ground with a jet mill to obtain a fine powder (also referred to as microparticle).

Further, the ground fine powder may be washed by the same method as that described in a method of drying in water in a method of preparing a microcapsule (I), lyophilized and further warmed and dried.

The thus obtained microcapsule or fine powder can achieve release of a drug corresponding to a decreasing rate of a lactic acid-glycolic acid polymer used.

The sustained-release composition of the present invention may be any form such as a microsphere, a microcapsule or a fine powder (microparticle), and a microcapsule is suitable.

The sustained-release composition of the present invention may be used as it is or the composition as a raw material may be formulated into a variety of dosage forms, and may be administered as an injectable agent or an implantable agent for intravenous, subcutaneous and intra-organ administration, as a transmucosal agent, an oral agent (for example, capsule (for example, hard capsule, soft capsule and the like)), solid preparations such as a granule, a powder and the like, or liquid agent such as a syrup agent, an emulsion, a suspension and the like for nasal, rectal or uterine administration.

For example, for formulating the sustained-release composition of the present invention into an injectable agent, it is formulated into an aqueous suspension together with a dispersant (for example, surfactants such as Tween 80, HCO-60 and the like, and polysaccharides such as sodium hyaluronate, carboxymethylcellulose, sodium arginate and the like), a preservative (for example, methylparaben and propylparaben), an isotonic (sodium chloride, mannitol, sorbitol, glucose and proline), or it is dispersed into an oily suspension together with a plant oil such as sesame oil or corn oil to obtain a sustained-release injection agent which can be actually used.

The particle diameter of a sustained-release composition of the present invention may be, when used as a suspension injection agent, in such a range that satisfies a dispersion degree and the needle penetrating property. For example, an average particle diameter is a range of about 0.1 to 300 μm, preferably about 0.5 to 150 μm, more preferably about 1 to 100 μm.

In order to formulate a sustained-release composition of the present invention into an aseptic preparation, methods include, but are not limited to a method of performing all steps aseptically in preparation, a method of sterilizing with gamma-ray, a method of adding an antiseptic and the like.

Since a sustained-release composition of the present invention of low toxicity, it can be used as a safe medicine for a mammal (for example, human being, cow, pig, dog, cat, mouse, rat, rabbit and the like), the dose of sustained-release composition of the present invention can vary depending on the type and content of the physiologically active substance, the dosage form, duration time of release of physiologically active substance, target disease and subject animal and effective amount of a physiologically active substance. A single dosage of physiologically active substance can be preferably selected appropriately from a range of about 0.01 mg to 10 mg/kg weight, more preferably about 0.05 mg to 5 mg/kg weight per adult, for example, when used in a sustained-release preparation for a six months preparation.

A single dose of a sustained-release composition can be preferably selected appropriately from about 0.05 mg to 50 mg/kg weight, more preferably about 0.1 mg to 30 mg/kg weight per adult.

Administration time can be appropriately selected depending on the type and content of a physiologically active substance as a basis, dosage form, duration time of release of a physiologically active substance, target disease and a subject animal, such as once every few weeks, once per month, once every few months (for example, three months, four months, six months etc) and the like.

A sustained-release composition of the present invention can be used as an agent for preventing or treating a variety of diseases depending on the type of physiologically active substance contained therein and, for example, when a physiologically active substance is an LH-RH derivative, it can be used for preventing or treating hormone dependent diseases, in particular, sex hormone dependent cancers (for example, prostate cancer, uterine cancer, breast cancer, pituitary gland tumor and the like), sex hormone dependent diseases such as prostatomegaly, endometriosis, hysteromyoma, precocious puberty, dysmenorrhea, amenorrhea, premenstrual syndrome, multilocular ovary syndrome and the like, as an agent for preventing recurrence of breast cancer after the operation for premenopausal breast cancer, as an agent for preventing or treating Alzheimer's disease or autoimmune diseases, and as a contraceptive (or, an agent for preventing or treating infertility, when the rebound activity after cease of administration is utilized). Further, it can also be used as an agent for preventing or treating benign or malignant tumors which are known to be sex hormone independent but sensitive to LH-RH.

Therefore, hormone dependent diseases, in particular, sex hormone dependent cancers (for example, prostate cancer, uterine cancer, breast cancer, pituitary gland tumor and the like), sex hormone dependent diseases such as prostatomegaly, endometriosis, hysteromyoma, precocious puberty, dysmenorrhea, amenorrhea, premenstrual syndrome, multilocular ovary syndrome and the like can be prevented or treated; and pregnancy can be prevented by administering to a mammal an effective dose of the treating or preventing agent according to this invention, and also recurrence of breast cancer after the operation for premenopausal breast cancer can be prevented thereby.

EXAMPLES

The present invention will be explained more specifically by way of Examples, Comparative Examples and Experimental Examples but the present invention is not limited by them.

Example A1

10 g of a lactic acid-glycolic acid copolymer, having a weight average molecular weight of 9700 and a number average molecular weight of 5030, synthesized by dehydration polycondensation of lactic acid and glycolic acid is dissolved in 100 mL of acetone, and 40 mL of purified water is added dropwise while stirring, to precipitate a polymer. The solution other than the precipitated glutinous starch syrup-like polymer is removed by decantation, and the resulting polymer is dried under vacuum. The polymer after drying has a yield of 8.37 g, a weight average molecular weight of 10500, and a number average molecular weight of 6700.

Example A2

4.87 g of the polymer obtained in Example A1 is dissolved in 8.03 g of dichloromethane into an oily phase. The oily phase is mixed into an aqueous phase in which 0.597 g of acetate of Peptide A is dissolved in 0.6 mL of purified water, which is primarily-emulsified at 25000 rpm using a Polytron to obtain a W/O emulsion. This W/O emulsion is added to 1000 mL of an 0.1% aqueous polyvinyl alcohol solution at 15° C., which is converted into a W/O/W emulsion at 7000 rpm using a homomixer. The microcapsule is solidified by desolvation with a propeller stirrer over three hours, then microcapsules which have passed through a 200 mesh sieve are recovered, and lyophilized after 0.48 g of mannitol has been added. After lyophilization, the yield of the resulting microcapsule is 3.92 g and the content of Peptide A is 10.18%.

Comparative Example A1

A microcapsule obtained using a lactic acid-glycolic acid copolymer of Example A1 according to the same manner as that of Example A2 has a yield of 3.97 g, and a content of Peptide A of 9.50%.

Experimental Example A1

Microcapsules obtained in Example A2 and Comparative Example A1 were dispersed in 0.3 ml of a dispersing medium (distilled water in which 0.25 mg of carboxymethylcellulose, 0.5 mg of Polysorbate 80 and 25 mg of mannitol are dissolved) at an amount of 2.25 mg in terms of Peptide A, which were administered to a male SD rat, 7 weeks old, in the back subcutaneously with a 22 G injection needle, respectively. A prescribed time after administration, rats were slaughtered, microcapsules remaining in the administration site was removed, and Peptide A remaining in it was quantitated, which was divided by each initial content to obtain a remaining rate as shown in Table 1. Further, Mw/Mn of polymers used in Example A2 and Comparative Example A1 are described in Table.

TABLE 1

|  | Comparative Example A1 | Example A2 |
|---|---|---|
| Mw/Mn | 1.93 | 1.57 |
| 1 day | 84.64% | 91.17% |
| 2 week | 32.2% | 54.31% |
| 4 week | 2.54% | 10.28% |

It is apparent from Table 1, that when a polymer used in Example A2 and having Mw/Mn of 1.90 or lower rendered by acetone treatment is used to prepare a microcapsule, the initial release amount of Peptide A from the microcapsule is suppressed, and sustained release over a long term of four weeks is ensured.

Example A3

185.7 g of a lactic acid-glycolic acid copolymer having a weight average molecular weight of 10600 and a number average molecular weight of 6600 was dissolved in 300.1 g of dichloromethane, and the temperature was adjusted to 29.5° C. 330.2 g was weighed from this organic solvent solution, then mixed with an aqueous solution which had been obtained by dissolving 15.62 g of acetate of Peptide A in 15.31 g of distilled water which had been warmed to 54.3° C., and stirred for 1 minute to obtain a crude emulsion, which was next emulsified under the conditions of 10,000 rpm for two minutes using a homogenizer to form a W/O emulsion. Then, this W/O emulsion was cooled to 17.8° C., poured into 25 liters of a 0.1% (w/w) aqueous polyvinyl alcohol (EG-40, manufactured by Nihongoseikagaku) solution which had been adjusted to 17.9° C. in advance, for 1 minute and 16 seconds, and stirred at 7,005 rpm using HOMOMIC LINE FLOW (manufactured by Tokushukika) to obtain a W/O/W emulsion. This W/O/W emulsion was stirred for 3 hours to volatilize dichloromethane or diffuse dichloromethane into an external aqueous phase, an oily phase was solidified, filtered through a sieve having 75 µm opening, and a microcapsule was settled continuously at 2,000 rmp using a centrifuge (H-600S, manufactured by Kokusanenshinki) and collected. The collected microcapsule was dispersed again in a small amount of distilled water, filtered through a sieve having 90 µm opening, which was dissolved by addition of 17.2 g of mannitol and lyophilized to obtain a powder. The microcapsule had a recovery rate of 76.4% and a content of Peptide A in the microcapsule of 8.79%.

Experimental Example A2

About 26 mg of a microcapsule described in Example A3 was dispersed in 0.3 ml of a dispersing medium (distilled water in which 0.15 mg of carboxymethylcellulose, 0.3 mg of Polysorbate 80 and 15 mg of mannitol are dissolved), which was administered to a male SD rat, 7 weeks old, in the back subcutaneously with a 22 G injection needle. A prescribed time after administration, the rat was slaughtered, microcapsule remaining in the administration site was removed, Peptide A in it was quantitated, which was divided by each initial content to obtain a remaining rate as shown in Table 2.

TABLE 2

|  | Time | | | | | |
|---|---|---|---|---|---|---|
|  | 1 day | 1 week | 2 weeks | 3 weeks | 4 weeks | 5 weeks |
| Remaining rate | 90.29% | 68.06% | 36.63% | 12.75% | 4.48% | 1.12% |

As apparent from Table 2, even when preparation was scaled up, although the microcapsule described in Example A3 contains a physiologically active substance at a high content, the remaining rate of a physiologically active substance one day after administration is as remarkably high as 90%. Therefore, when an Mw/Mn ratio of a polymer is a low value as about 1.6, the effect of considerably suppressing initial excessive release of a physiologically active substance is exerted. In addition, this microcapsule achieves release of the physiologically active substance at a constant rate over a long period of time.

Example B1

197.7 g of a lactic acid-glycolic acid copolymer having a weight average molecular weight of 12600 and a number average molecular weight of 6400 was dissolved in 320.1 g of dichloromethane, press-filtered using a 0.2 µm filter (EM-FLOW, DFA4201FRP), and the temperature was adjusted to about 30.0° C. 330.1 g was weighed, mixed with an aqueous solution which had been obtained by dissolving 15.68 g of acetate of Peptide A in 15.31 g of distilled water and had been warmed to 56.0° C., stirred for 1 minute to obtain a crude emulsion, which was then emulsified under the condition of 10,000 rpm for two minutes to obtain a W/O emulsion. Then, this W/O emulsion was cooled to 18.2° C., poured into 25 liters of a 0.1% (w/w) polyvinyl alcohol (EG-40, manufactured by Nihongoseikagaku) which had been adjusted to 18.4° C. in advance, for 1 minute and 46 seconds, stirred at 7,007 rpm using HOMOMIC LINE FLOW (manufactured by Tokushukika) to obtain a W/O/W emulsion. This W/O/W emulsion was stirred for 3 hours to volatilize dichloromethane or diffuse it into an external aqueous phase, then the oily phase was solidified, filtered using a seive having 75 µm opening, and microcapsule was continuously settled at 2,000 rpm using a centrifuge (H-600S, manufactured by Kokusanenshinki) and collected. The collected microcapsule was dispersed again in a small amount of distilled water, filtered using a seive having 90 µm opening, then dissolved by addition of 17.2 g of mannitol and lyophilized to obtain a powder. The microcapsule had a recovery rate of 73.47% and a content of Peptide A in a microcapsule of 8.43%.

Experimental Example B1

About 26.7 mg of the microcapsule described in Example B1 was dispersed in 0.3 mg of dispersing medium (distilled water in which 0.15 mg of carboxymethylcellulose, 0.3 mg of Polysorbate 80, and 15 mg of mannitol were dissolved), and administered to a male SD rat, 7 weeks old, in the back subcutaneously with a 22 G injection needle. A prescribed time after administration, the rat was slaughtered, and microcapsule remaining at the administration site, and Peptide A in it was quantitated, which was divided by each initial content to obtain a remaining rate as shown in Table 3.

TABLE 3

|  | Time | | | | |
| --- | --- | --- | --- | --- | --- |
|  | 1 day | 1 week | 2 weeks | 3 weeks | 4 weeks | 5 weeks |
| Remaining rate | 82.43% | 68.33% | 47.07% | 23.58% | 9.05% | 2.08% |

As apparent from Table 3, microcapsule described in Example B1 could contain a physiologically active substance at a high content even when gelatin was not included, and remarkably suppressed initial release of a physiologically active substance and, this microcapsule released a physiologically active substance over a long period of time.

Experimental Example B2

About 44.6 mg of a microcapsule described in Example B1 was dispersed in 11.0 ml of a dispersing medium (distilled water in which 0.15 mg of carboxymethylcellulose, 0.3 mg of Polysorbate 80, and 15 mg of mannitol were dissolved), which was administered to a beagle, weighing 7 to 12 kg, in the back subcutaneously with a 23 G injection needle. A prescribed time after administration, blood was taken from a forefoot vein, the concentrations of Peptide A and testosterone were quantitated, and the results are shown in Table 4.

TABLE 4

|  | Time | | | | |
| --- | --- | --- | --- | --- | --- |
|  | 1 day | 1 week | 2 week | 3 week | 4 week | 5 week |
| Peptide A | 2.21 | 0.398 | 0.525 | 0.433 | 0.603 | 0.358 |
| Testosterone | 2.79 | 0.57 | 0.35 | 0.35 | 0.30 | 0.39 |

As apparent from Table 4, a microcapsule described in Example B1 releases a physiologically active substance for a long period of time, and maintained the blood concentration of the physiologically active substance. In addition, the activity of the physiologically active substance released into blood was not lost and drug efficacy was retained.

INDUSTRIAL APPLICABILITY

A sustained-release preparation of the present invention, having a ratio of weight average molecular weight to number average molecular weight of PLGA as a base of about 1.90 or lower, or using a lactic acid-glycolic acid polymer having weight average molecular weight of about 11,600 to about 14,000 or a salt thereof as a base, contains a physiologically active substance in high content even when gelatin is not included, and suppresses initial excessive release of physiologically active substance and, thus, can achieve a stable release rate over about one month.

That is, the preparation according to this invention has such useful effects that the manufacturing process and cost can be reduced because there is no need for using a drug retaining substance such as gelatin and a thickening agent, resulting reduced additives, and that the preparation can contain a drug at a high concentration without using a drug retaining substance and a thickening agent; a sustained-release composition which releases a drug over at least two weeks can be produced; and the preparation having high stability can be produced owing to the increase of glass transition temperature.

The invention claimed is:

1. A process for producing a lactic acid-glycolic acid polymer having weight average molecular weight of 8,000 to 15,000 and having a ratio of weight average molecular weight to number average molecular weight of 1.40 to 1.90, and having a molar ratio of lactic acid to glycolic acid of from 100:0 to 40:60, or a salt thereof, which comprises adding water to an organic solvent containing a lactic acid-glycolic acid polymer having weight average molecular weight of 5,000 to 15,000 at a ratio of 24 to 40 (ratio by volume) relative to 100 of the organic solvent.

2. The process for producing a polymer according to claim 1, wherein the organic solvent is hydrophilic.

3. The process for producing a polymer according to claim 2, wherein the organic solvent is acetone.

4. The process for producing a polymer according to claim 1, wherein the ratio of water relative to 100 of the organic solvent is 40 (ratio by volume).

* * * * *